(12) United States Patent
Biedermann et al.

(10) Patent No.: US 8,795,336 B2
(45) Date of Patent: Aug. 5, 2014

(54) BONE ANCHORING DEVICE AND STABILIZATION DEVICE FOR BONE PARTS OR VERTEBRAE COMPRISING SUCH A BONE ANCHORING DEVICE

(75) Inventors: Lutz Biedermann, VS-Villingen (DE); Jürgen Harms, Karlsruhe (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 213 days.

(21) Appl. No.: 12/571,299

(22) Filed: Sep. 30, 2009

(65) Prior Publication Data

US 2010/0087865 A1  Apr. 8, 2010

Related U.S. Application Data

(60) Provisional application No. 61/103,858, filed on Oct. 8, 2008.

(30) Foreign Application Priority Data

Oct. 8, 2008  (EP) ..................... 08017644

(51) Int. Cl.
*A61B 17/70* (2006.01)
*A61B 17/88* (2006.01)

(52) U.S. Cl.
USPC ........... 606/264; 606/257; 606/267; 606/279; 606/261

(58) Field of Classification Search
USPC ............... 606/264–266, 250–261, 275–279
See application file for complete search history.

(56) References Cited

U.S. PATENT DOCUMENTS 3,997,138 A * 12/1976 Crock et al. ................ 248/67.5
5,704,936 A * 1/1998 Mazel ........................ 606/254
(Continued)

FOREIGN PATENT DOCUMENTS

DE  198 48 715 C1   8/2000
EP   1 800 613 A1   6/2007
(Continued)

OTHER PUBLICATIONS

European Search Report for European Application No. 08017644.9, Applicant, Biedeunann Motech GmbH, European Search Report dated Jan. 29, 2009 and mailed Feb. 5, 2009 (9 pgs.)

*Primary Examiner* — Ellen C Hammond
*Assistant Examiner* — Jacqueline Johanas
(74) *Attorney, Agent, or Firm* — Christie, Parker & Hale, LLP

(57) ABSTRACT

A stabilization device for bone parts or vertebrae includes two bone anchoring devices for anchoring in the bone parts or vertebrae. At least one of the bone anchoring devices includes an anchoring element with an anchoring section for anchoring in a bone part or a vertebra and a head, and a receiving part for receiving a stabilization rod. The receiving part has a seat for receiving the head so that the head can pivot with respect to the receiving part. The stabilization device includes a first pressure element which is movable in the receiving part so that it can be pressed onto the head to lock the angular position of the head. The stabilization device includes at least two stabilization rod sections, and at least two guiding channels within the receiving part which have a distance from each other for guiding through the at least two stabilization rod sections so that the rod sections do not touch each other.

27 Claims, 5 Drawing Sheets

(56) References Cited

U.S. PATENT DOCUMENTS

| | | | |
|---|---|---|---|
| 5,797,911 A | 8/1998 | Sherman et al. | |
| 6,206,879 B1 | 3/2001 | Marnay et al. | |
| 7,326,210 B2* | 2/2008 | Jahng et al. | 606/86 A |
| 7,722,651 B2* | 5/2010 | Kwak et al. | 606/265 |
| 7,766,915 B2* | 8/2010 | Jackson | 606/86 A |
| 7,935,134 B2* | 5/2011 | Reglos et al. | 606/257 |
| 7,942,907 B2* | 5/2011 | Richelsoph | 606/257 |
| 7,951,170 B2* | 5/2011 | Jackson | 606/257 |
| 8,192,468 B2* | 6/2012 | Biedermann et al. | 606/257 |
| 8,394,133 B2* | 3/2013 | Jackson | 606/302 |
| 2004/0039388 A1 | 2/2004 | Biedermann et al. | |
| 2004/0049190 A1 | 3/2004 | Biedermann et al. | |
| 2004/0097942 A1* | 5/2004 | Allen et al. | 606/72 |
| 2004/0111088 A1 | 6/2004 | Picetti et al. | |
| 2004/0172024 A1* | 9/2004 | Gorek | 606/61 |
| 2004/0254577 A1* | 12/2004 | Delecrin et al. | 606/61 |
| 2005/0010215 A1* | 1/2005 | Delecrin et al. | 606/61 |
| 2005/0101956 A1* | 5/2005 | Simonson | 606/61 |
| 2005/0154388 A1* | 7/2005 | Roussouly et al. | 606/61 |
| 2005/0171537 A1 | 8/2005 | Mazel et al. | |
| 2005/0277931 A1* | 12/2005 | Sweeney et al. | 606/61 |
| 2006/0036240 A1* | 2/2006 | Colleran et al. | 606/61 |
| 2006/0064090 A1* | 3/2006 | Park | 606/61 |
| 2006/0247779 A1* | 11/2006 | Gordon et al. | 623/17.15 |
| 2006/0271046 A1* | 11/2006 | Kwak et al. | 606/61 |
| 2007/0055244 A1* | 3/2007 | Jackson | 606/61 |
| 2007/0118124 A1 | 5/2007 | Biedermann et al. | |
| 2007/0225708 A1 | 9/2007 | Biedermann et al. | |
| 2007/0233085 A1 | 10/2007 | Biedermann et al. | |
| 2007/0288008 A1* | 12/2007 | Park | 606/61 |
| 2007/0288094 A1* | 12/2007 | Krishna et al. | 623/17.15 |
| 2008/0183212 A1* | 7/2008 | Veldman et al. | 606/254 |
| 2008/0183213 A1* | 7/2008 | Veldman et al. | 606/257 |
| 2008/0195154 A1* | 8/2008 | Brown et al. | 606/257 |
| 2008/0262545 A1* | 10/2008 | Simonson | 606/247 |
| 2008/0300633 A1* | 12/2008 | Jackson | 606/257 |
| 2009/0204156 A1* | 8/2009 | McClintock et al. | 606/278 |
| 2010/0069962 A1* | 3/2010 | Harms et al. | 606/254 |
| 2010/0160967 A1* | 6/2010 | Capozzoli | 606/256 |
| 2010/0204736 A1* | 8/2010 | Biedermann et al. | 606/264 |
| 2010/0318130 A1* | 12/2010 | Parlato et al. | 606/254 |
| 2010/0331887 A1* | 12/2010 | Jackson et al. | 606/264 |
| 2011/0160774 A1* | 6/2011 | Malek | 606/255 |
| 2011/0301643 A1* | 12/2011 | Jahng | 606/254 |

FOREIGN PATENT DOCUMENTS

| | | |
|---|---|---|
| EP | 1 800 614 A1 | 6/2007 |
| FR | 2 863 860 A1 | 6/2005 |
| WO | WO 03/034930 A1 | 5/2003 |
| WO | WO 03/045261 A1 | 6/2003 |
| WO | WO 2005/058173 A1 | 6/2005 |
| WO | WO 2008/036578 A2 | 3/2008 |

\* cited by examiner

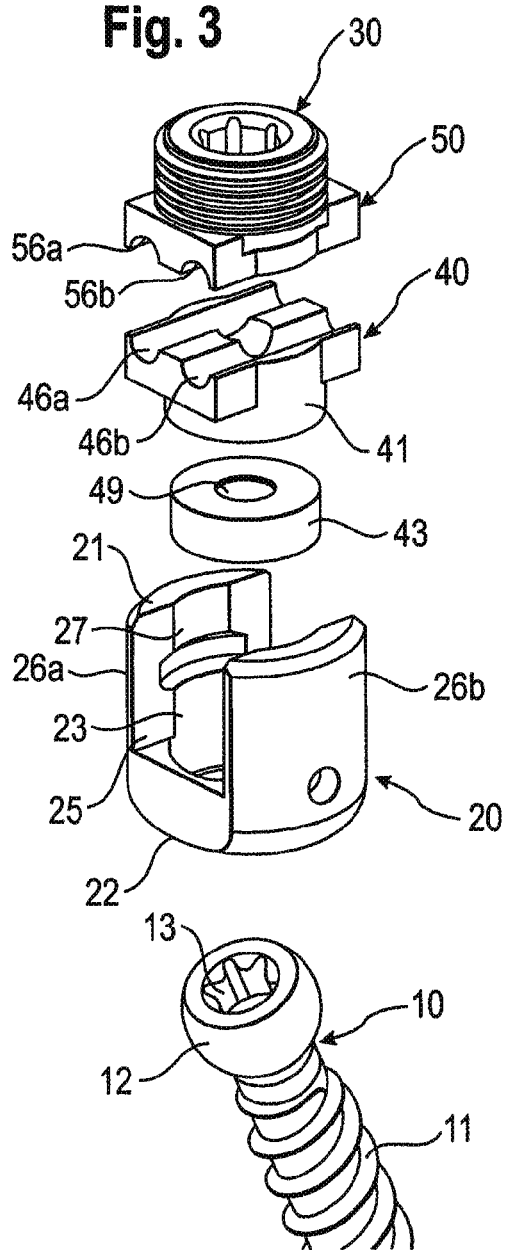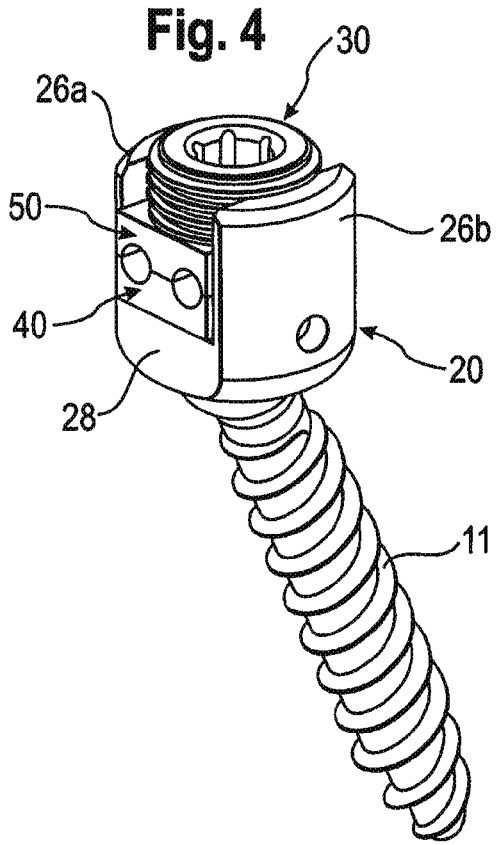

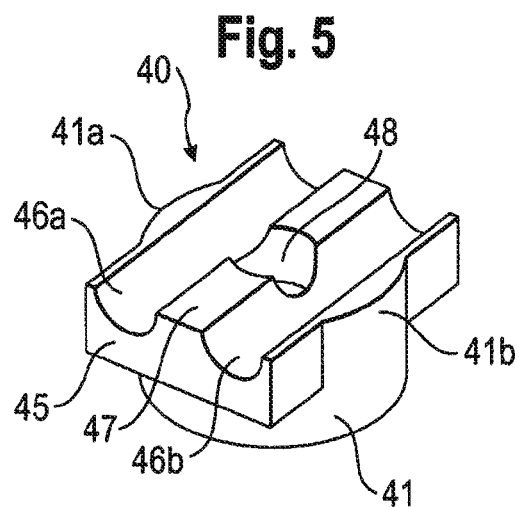
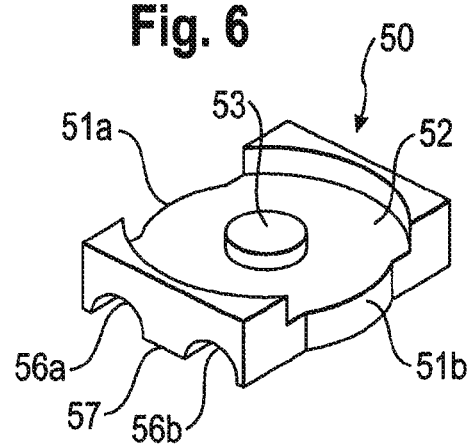
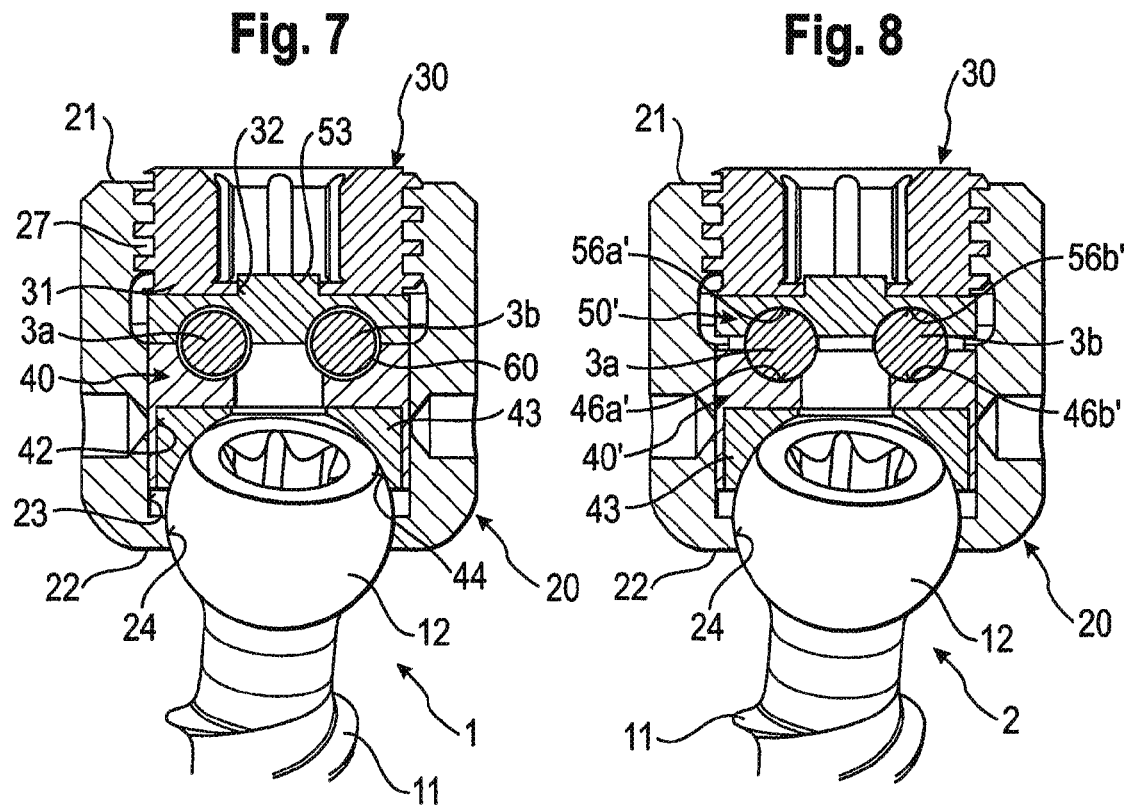

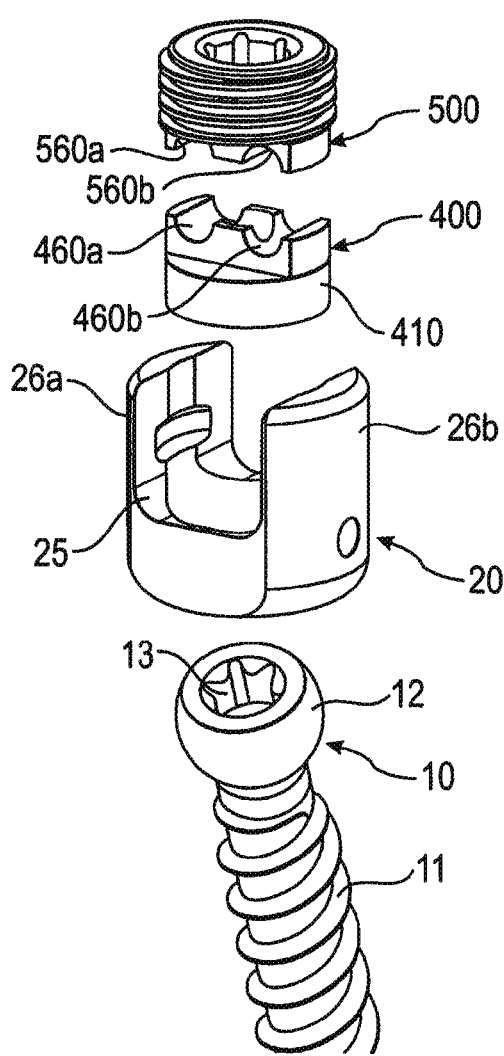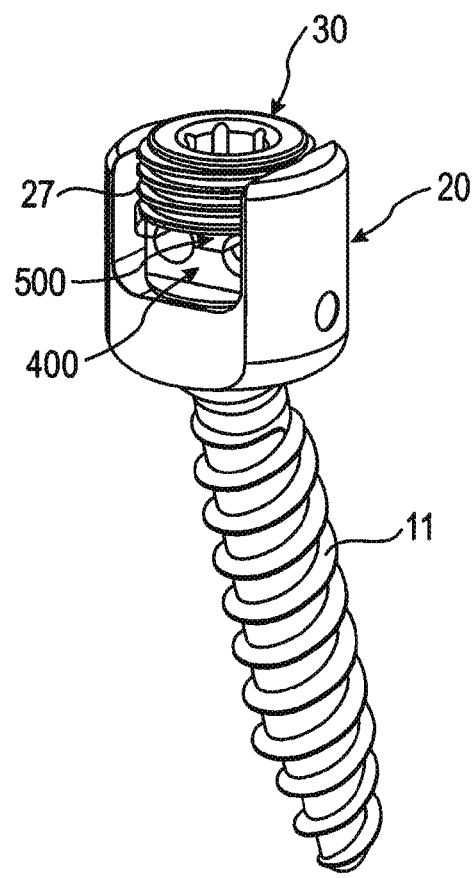

BONE ANCHORING DEVICE AND STABILIZATION DEVICE FOR BONE PARTS OR VERTEBRAE COMPRISING SUCH A BONE ANCHORING DEVICE

CROSS-REFERENCE TO RELATED APPLICATION(S)

The present application claims the benefit of U.S. Provisional Patent Application Ser. No. 61/103,858, filed Oct. 8, 2008, the contents of which are hereby incorporated by reference in their entirety, and claims priority from European Patent Application EP 08 017 644.9, filed Oct. 8, 2008, the contents of which are hereby incorporated by reference in their entirety.

BACKGROUND

The invention relates to a bone anchoring device, in particular to a polyaxial bone screw which is connected to two stabilization rods and to a stabilization device having such a bone anchoring device, in particular for the stabilization of the spinal column.

A dynamic stabilization device for bones, in particular for vertebrae, is described in US 2004/0049190 A1. The stabilization device includes two bone anchoring elements, at least one of which is a polyaxial bone screw and a rigid rod with a longitudinal axis connecting them. An elastic element is inserted between the two bone anchoring elements. The elastic element acts on the bone anchoring elements to exert a force in a direction of the longitudinal axis. One of the bone anchoring elements is fixedly connected to the rod to prevent translational movement of the rod and the other bone anchoring element is slidably connected to the rod.

EP 1 800 614 A1 describes a dynamic stabilization device for bones or for vertebrae having at least two bone anchoring elements and at least one connection element in the form of an elastic loop connecting the bone anchoring elements. In one embodiment, the bone anchoring element is in the form of a polyaxial bone screw having a receiving part which accommodates to two elastic loops each of which can be connected to a second bone anchoring element.

Based on the foregoing, there is a need to provide a bone anchoring device and a stabilization device comprising such a bone anchoring device which allows the dynamic stabilization of bone parts or vertebrae and which allows a variable design of elastic properties of the dynamic stabilization device.

SUMMARY

The provision of a modular double-rod, i.e. two rods, allows to design the bone anchoring device more compact in terms of the height of the bone anchoring device, since each rod can be designed smaller than a single rod. The low profile cross-section of two rods compared to one single rod has also the advantage that the stiffness of the rods is enhanced. The stability in view of bending or torsional loads of the double-rod system is also enhanced.

The dynamic properties of the stabilization device can be adjusted by selecting appropriate rods and/or adjusting the sliding motion of the rods by stops and/or dampening elements. The dynamic properties of the rods can vary. For example the rods can have the same or different elastic properties. They can be made of the same or different material.

BRIEF DESCRIPTION OF THE DRAWINGS

FIG. 3 shows an exploded view of the bone anchoring device according to a first embodiment.

FIG. 4 shows a perspective view of the bone anchoring device of FIG. 3 in an assembled state.

FIG. 5 shows a perspective view from the side of the first pressure element in a first embodiment.

FIG. 6 shows a perspective view of the second pressure element in a first embodiment.

FIG. 7 shows a partially sectional view of the bone anchoring device with the first and second pressure element according to the first embodiment.

FIG. 8 shows a partially sectional view of the bone anchoring device with the first and second pressure element according to a second embodiment.

FIG. 9 shows an exploded perspective view of the bone anchoring device with a first and second pressure element according to a third embodiment.

FIG. 10 shows a perspective view of the bone anchoring device of FIG. 9 in an assembled state.

DETAILED DESCRIPTION

Figure 11:
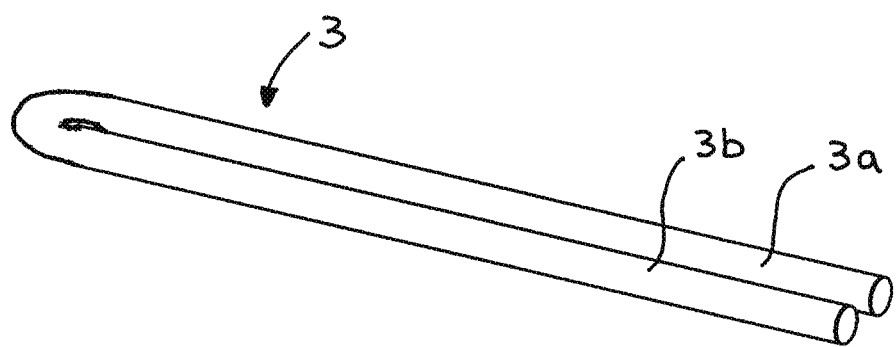
FIG. 11 shows a perspective view of a rod according to another embodiment.

The invention is now described in detail with reference to the embodiment of the stabilization device shown in FIGS. 1 to 8. The stabilization device includes a first polyaxial pedicle screw 1, a second pedicle screw 2 and two rods 3a, 3b connecting them for stabilizing two adjacent vertebrae. The two rods 3a, 3b may be separate rods as shown in FIG. 2. Alternatively, as shown in FIG. 11, the rods 3a, 3b may be connected or formed in one-piece to define a single rod 3.

On each rod a spring element 4a, 4b is provided and the rods 3a, 3b are connected by rod connectors 5, 6. The rods 3a, 3b are fixedly clamped in the second pedicle screw 2 and can slide through the first pedicle screw 1 as shown by the arrows. The sliding motion is limited by means of the rod connector 6 which connects the free ends of the rods 3a, 3b and acts as a stop. The springs 4a, 4b and the rod connector 5 limit the sliding motion of the rods 3a, 3b relative to the first pedicle screw 1 in the direction of the second pedicle screw 2. The springs provide elastic dampening. The rod connectors 5, 6 are sleeve shaped with two channels 5a, 5b, 6a, 6b, respectively, for guiding through the rods 3a, 3b. The distance of the channels corresponds to the distance of the rods in which they are guided through the pedicle screws. The rod connectors 5, 6 connect the rod 3a, 3b by means of a press-fit connection i.e. the diameter of the channels is selected such that the rods are firmly connected. The rod connectors 5, 6 can be made of an elastomer material or any other body compatible material.

The springs 4a, 4b in this embodiment are shown as helical springs encompassing the rods 3a, 3b like sleeves. They can be made of any body compatible material, in particular of titanium, nickel titanium alloys, for example nitinol, or other materials.

The rods 3a, 3b exhibit a flexibility under forces having a component perpendicular to the rod axis, such as bending forces. For this purpose the rods are made of non-compressible materials, such as stainless steel, titanium, nickel titanium alloys, such as nitinol, PEEK or carbon reinforced PEEK or other body compatible materials.

It should be noted that the rod connectors and the springs are only examples for the function of connecting the two rods, providing a stop and providing a dampening to the sliding motion.

Next, the first pedicle screw 1 will be described in detail with reference to FIGS. 3 to 7. The pedicle screw 1 comprises a screw element 10 with a threaded shank 11 and a spherically segment-shaped head 12. At the free end of the head 12 a recess 13 is provided for engagement with a tool. The pedicle screw 1 further comprises a receiving part 20 with a first end 21 and a second 22 and a coaxial bore 23 extending from the first end in the direction of the second end. At the second end 22 the bore 23 tapers to provide an opening and a seat 24 for the screw, head 12 as shown in particular in FIG. 7.

The receiving part 20 further comprises a recess 25 extending from the first end 21 in the direction of the second end 22 which provides a channel through the receiving part in a direction perpendicular to the bore axis of bore 23 for guiding through the rods 3a, 3b. The recess provides two free legs 26a, 26b. Near the first end 21 the free legs 26a, 26b have an internal thread 27 for cooperation with a fixation screw 30. The screw element 10 and the receiving part 20 as well as the fixation screw 30 are made of a rigid body compatible material, such as a body compatible metal like stainless steel or titanium or a titanium alloy, such as nitinol.

For locking the head 12 and in consequence the angular position of the screw element 10 within the seat 24 of the receiving 20 a first pressure element 40 and a second pressure element 50 are provided. The first pressure element 40 and the second pressure element 50 also form guiding elements for guiding the rods 3a, 3b through the receiving part 20. The first pressure element 40 has a substantially cylindrical body part 41 which is sized such that the first pressure element 40 can be inserted in the receiving part and moved in an axial direction within the bore 23. At its side facing the head 12 of the screw element the first pressure element 40 comprises a cylindrical recess 42 shown in FIG. 7 in which a cylindrical insert 43 is provided. The insert 43 has on its side facing the head 12 of the screw element a spherical recess 44 the radius of which fits to the radius of spherical head 12 of the screw element.

The first pressure element 40 further comprises a cuboid body part 45 which is shaped so as to fit in the recess 25 of the receiving part 20 as shown in particular in FIGS. 3 and 4. The width of the body part 45 corresponds to the width of the recess 25 and the length is selected such that the first pressure element is flush with the outer surface 28 of the receiving part 20 as shown in FIG. 4. On its side opposite to the recess 42 the cuboid body part includes two cylinder segment-shaped recesses 46a, 46b the cylinder radius of which is slightly larger than the radius of the rods 3a, 3b. The recesses 46a, 46b extend perpendicular to the axis of the coaxial bore 23 of the receiving part 20. The recesses 46a, 46b form channels for receiving the rods 3a, 3b. Since the recesses 46a, 46b are spaced apart from each other a rib 47 is formed between them. The depth of the recesses 46a, 46b is preferably slightly larger than the radius of the rods 3a, 3b. The first pressure element 40 also has a coaxial bore 48 for providing access to the head 12 of the screw element with a tool. Similarly, the cylindrical insert 43 has a coaxial bore 49. The cylindrical body part 41 and the cuboid body part 25 are shown to be made in one piece so that cylindrical segment-shaped flanges 41a, 41b are provided on each side of the channel 46a, 46b. The flanges facilitate the guidance of the first pressure element 40 within the receiving part 20. The cuboid body part 45 prevents rotation of the first pressure element within the receiving part once the first pressure element is inserted into the recess 25.

The second pressure element 50 is substantially cuboid shaped with a width and length corresponding to that of the cuboid body part 45 of the first pressure element 40. Therefore, it also fits into the recess 25 of the receiving part. On its long sides it comprises two cylindrical segment-shaped flanges 51a, 51b corresponding to the flanges 41a, 41b of the first pressure element. On its side opposite to the first pressure element 40, the second pressure element 50 comprises a cylindrical recess 52 and a coaxial cylindrical projection 53 in which a corresponding ring-shaped projection 31 and a cylindrical recess 32 of the fixation screw 30 engage, as shown in FIG. 7. Thereby, the fixation screw 30 can be rotatably connected to the pressure element 50.

On its side facing the first pressure element, the second pressure element 50 comprises two longitudinal cylinder segment-shaped recesses 56a, 56b which are complementary in their size and distance to the channels 46a, 46b of the first pressure element. The channels 56a, 56b are spaced apart by a rib 57.

In the assembled state shown in FIG. 7 the first pressure element presses via the insert 43 onto the head 12. The second pressure element 50 presses onto the first pressure element 40 thereby providing closed channels for the rods 3a, 3b which are accommodated therein with a gap 60 to the wall of the channel. Since the fixation screw 30 is rotatably connected to the second pressure element, the fixation screw 30 can be tightened when the second pressure element 50 is inserted.

The first pressure element and the second pressure element can be made of a material which facilitates sliding of the rods 3a, 3b. For example, the pressure elements can be made of titanium or a nickel titanium alloy which is coated or of PEEK or carbon reinforced PEEK. The insert 43 is preferably made of the same material as the head 12 of the screw, for example of a body compatible metal. Instead of providing the insert 43 the first pressure element itself can have a spherical recess to press onto the head. Instead of providing the first and second pressure element of a material which facilitates sliding or which is coated or treated to facilitate sliding, the rods 3a, 3b themselves can have a surface which facilitates sliding, for example a coated or otherwise treated surface.

Figure 1:
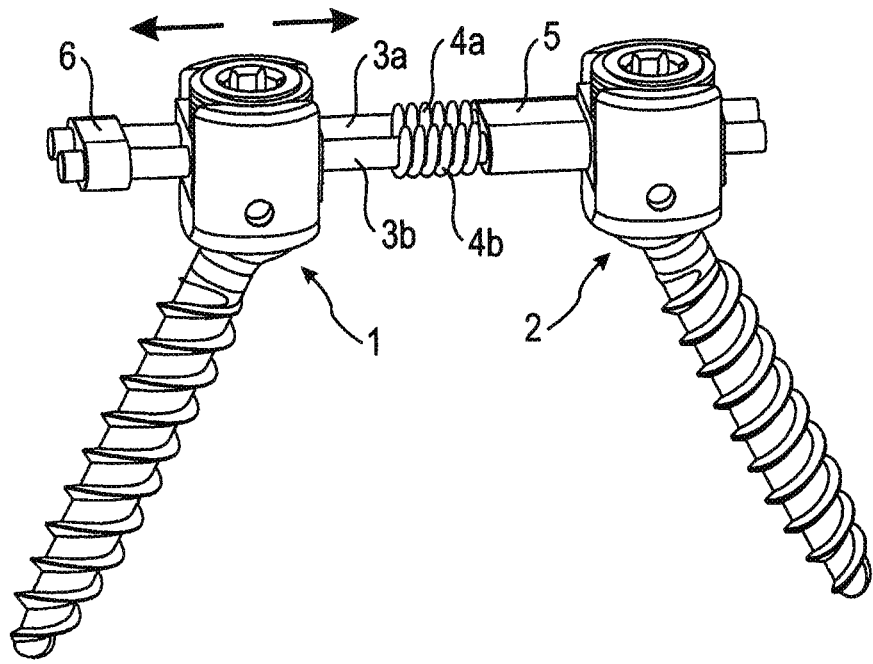
FIG. 1 shows a perspective side view of the stabilization device.
Figure 2:
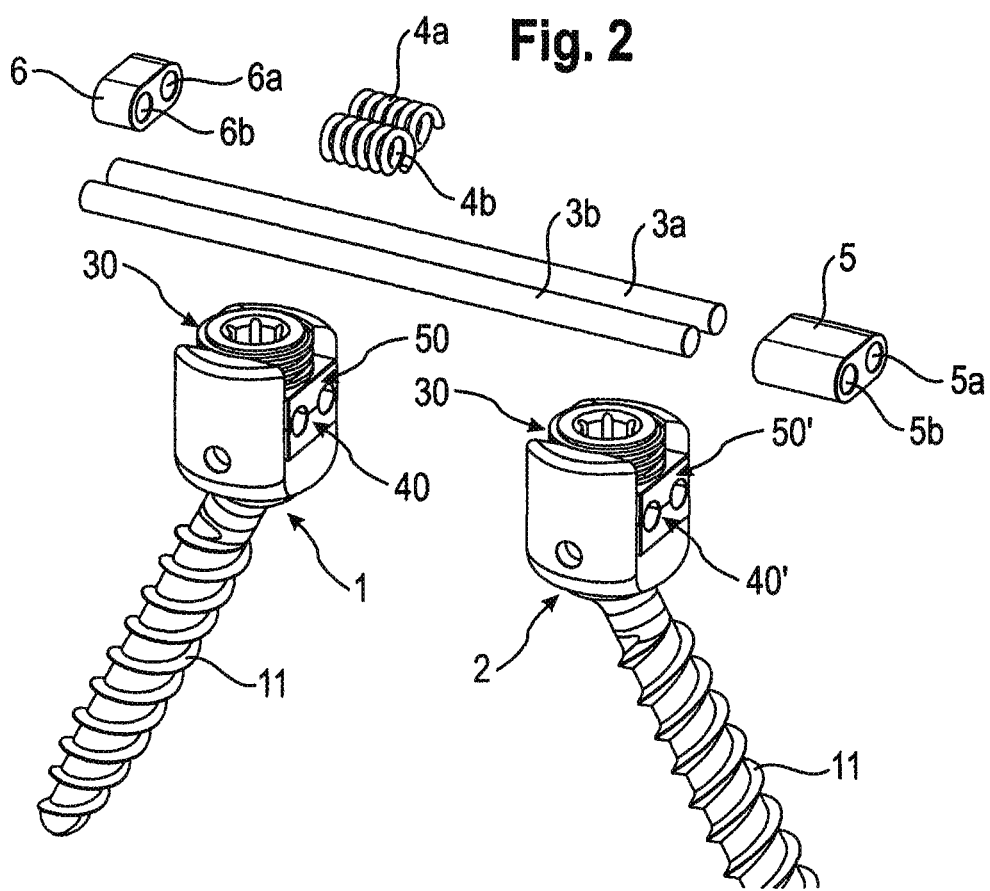
FIG. 2 shows a perspective exploded view of the stabilization device.

The second pedicle screw 2 shown in FIGS. 1, 2 and 8 differs from the first pedicle screw 1 in the design of the first and second pressure elements. All other parts are identical and have the same reference numerals. Therefore, the description thereof is not repeated. The shape of the first pressure element 40' and of the second pressure element 50' of the second pedicle screw 2 is the same as that of the first pressure element 40 and the second pressure element 50 of the first pedicle screw 1. However, the size of the channels 46a', 46b', 56a', 56b' is smaller than that of the channels of the first and second pressure element of the first pedicle screw. The radius of the channels is adapted to the radius of the rods 3a, 3b and depth of the channels is smaller than the radius of the rods 3a, 3b such that, as shown in FIG. 8, in the assembled state the rods 3a, 3b are clamped between the first pressure element 40' and the second pressure element 50'.

A second embodiment of the stabilization device is shown in FIGS. 9 and 10 without the rods. The second embodiment differs from the first embodiment described with reference to FIGS. 1 to 8 only in the shape of the first and second pressure elements 400, 500. The length of the channels 460a, 460b is smaller than the diameter of the cylindrical body part 410. Therefore, the first pressure element 400 and the second pressure element 500 are arranged completely within the cylindrical bore 23 of the receiving part.

Modifications of the above described embodiments are conceivable. For example, the pedicle screws and the design of the pressure elements can be such that more than two rods can be accommodated. It is possible to use rods with different elastic properties. It is sufficient, if one of the pressure elements has the channels for guiding the rods, however, it is advantageous if the rods are guided from below and from the top by the channels. The shape of the lower part of the first pressure element can be flat, however, a shape adapted to the shape of the head of the screw 12 is advantageous for distributing the pressure onto the head.

The fixation element can be a two-part fixation screw wherein the first screw element of a bushing type presses onto the first pressure element for locking of the head 12 and a second screw element of a set screw type arranged within the first screw element presses onto the second pressure element for fixation of the rods in the embodiment shown in FIG. 8.

The receiving part can be shaped as a top loader as shown in the figures or a bottom loader in which the screw element 10 is introduced from the bottom, i.e. the second end of the receiving part.

The shank of the screw element does not have to have a thread. It can be in the form of a hook, a nail or can have barb elements for anchoring in the bone.

The springs can be also provided adjacent the outer stop 6. It is also conceivable that the rods themselves have an axial elastic spring portion.

In use, first the screw elements of the pedicle screws 1, 2 which have been inserted into the receiving parts 20 are screwed into adjacent vertebrae. The first pressure elements can be preassembled so that after alignment of the receiving parts the rods 3a, 3b can be inserted into the receiving parts and the channels of the first pressure element, respectively. The rods 3a, 3b with the stops and the springs can be preassembled as well and can be inserted as a double-rod system. For specific clinical applications the first pedicle screw and the stop 6 points in the direction the patient's head. However, the arrangement of the pedicle screws depends on the specific clinical situation.

Next, after the receiving parts and the rods are aligned the angular position of the screw elements relative to the receiving parts is fixed by inserting the fixation screw together with the second pressure element and tightening the fixation screw. In the case of the second pedicle screw 2 as shown in FIGS. 1, 2 and 8 the rods 3a, 3b are fixed simultaneously with the screw head 12. In the case of the first pedicle screw only the head 12 of the screw element is fixed while the rods can still slide within the channels.

As shown in FIG. 1 the rods can slide through the receiving part of the first pedicle screw during flexion or extension of the spinal motion segment, whereby the sliding movement is limited by the rod connectors 6 and 5 acting as stops and dampened by the springs 4a, 4b. Simultaneously, the rods may experience bending forces and can bend to some extend provided by the flexibility of the material of the rods.

What is claimed is:

1. A bone anchoring device comprising:
   an anchoring element with an anchoring section for anchoring in a bone part or a vertebra and a head;
   a monolithic first stabilization rod and a monolithic second stabilization rod;
   a receiving part having a first end and a second end and a bore extending along an axis from the first end in the direction of the second end, wherein the receiving part has a seat in the bore for receiving the head so that the head is polyaxially pivotable with respect to the receiving part;
   a first pressure element movable in the bore of the receiving part and configured to press onto the head to lock the angular position of the head relative to the receiving part;
   wherein at least two guiding channels are provided within the bore of the receiving part for guiding the first stabilization rod and the second stabilization rod through the receiving part;
   wherein when the first stabilization rod and the second stabilization rod are guided through the receiving part with the guiding channels, the first stabilization rod and the second stabilization rod are entirely spaced apart from each other in the receiving part; and
   wherein when the angular position of the head relative to the receiving part is locked, the first stabilization rod and the second stabilization rod are slidably connected to the receiving part and are configured to contact the first pressure element.

2. The bone anchoring device of claim 1, wherein the guiding channels are provided in the first pressure element on a side facing away from the head.

3. The bone anchoring device of claim 1, further comprising a second pressure element configured to act directly onto one of the first pressure element and the rods.

4. The bone anchoring device of claim 3, wherein the second pressure element is movable in the bore.

5. The bone anchoring device of claim 3, wherein the channels are provided in the second pressure element.

6. The bone anchoring device of claim 1, wherein the channels are sized larger than the stabilization rods to allow the rods to slide therein.

7. The bone anchoring device of claim 6, wherein at least one of the surface of the channels and the surface of the rods are one of treated and made of a material which facilitates sliding.

8. The bone anchoring device of claim 1, further comprising a fixation element configured to fix the position of the head in the receiving part.

9. The bone anchoring device of claim 1, further comprising a connector connecting an end of the first stabilization rod to an end of the second stabilization rod.

10. The bone anchoring device of claim 1, further comprising a connector configured to connect the first stabilization rod and the second stabilization rod, the connector configured to be positioned outside of the bore and to be spaced apart from the free ends of the first and second stabilization rods, respectively.

11. The bone anchoring device of claim 1, further comprising a second anchoring element, a second receiving part, and a second pressure element, wherein at least two guiding channels are provided within a bore of the second receiving part for guiding the first stabilization rod and the second stabilization rod through the second receiving part, such that the first and second stabilization rods are connectable to the first and second receiving parts at the same time.

12. A stabilization device for stabilizing bone parts or vertebrae, the stabilization device comprising:
   a monolithic first stabilization rod;
   a monolithic second stabilization rod;
   a first bone anchoring device and a second bone anchoring device, each bone anchoring device comprising:
      an anchoring element with an anchoring section for anchoring in a bone part or a vertebra and a head;
      a receiving part having a seat for receiving the head so that the head is polyaxially pivotable with respect to the receiving part;
      a first pressure element movable in the receiving part and configured to press onto the head to lock the angular position of the head relative to the receiving part;
      wherein at least two guiding channels are provided within the receiving part for guiding the first stabilization rod and the second stabilization rod through the receiving part;
   wherein when the respective angular positions of the heads relative to the corresponding receiving parts of the bone anchoring devices are locked, the first stabilization rod and the second stabilization rod are fixedly connected to the first bone anchoring device, and the first stabilization rod and the second stabilization rod are slidably connected to the second bone anchoring device and are configured to contact the first pressure element of the second bone anchoring device.

13. The stabilization device of claim 12, wherein at least one stop is provided for limiting the sliding movement of the rods relative to the second bone anchoring device.

14. The stabilization device of claim 12, wherein each of the rods exhibits bending flexibility when a force component acts in a direction perpendicular to a rod axis.

15. The stabilization device of claim 12, wherein each of the rods comprises a spring element for dampening the sliding movement of the rods relative to the second bone anchoring device.

16. The stabilization device of claim 12, wherein for each of the bone anchoring devices, the guiding channels are provided in the first pressure element on a side facing away from the head.

17. The stabilization device of claim 12, wherein each of the bone anchoring devices further comprises a second pressure element configured to act directly onto one of the first pressure element of the bone anchoring device and the rods.

18. The stabilization device of claim 17, wherein the second pressure element of each bone anchoring device is movable in the receiving part of the bone anchoring device.

19. The stabilization device of claim 17, wherein the channels of each bone anchoring device are provided in the second pressure element of the bone anchoring device.

20. The stabilization device of claim 12, wherein the channels of the second bone anchoring device are sized larger than the stabilization rods to allow the rods to slide therein.

21. The stabilization device of claim 12, wherein the channels of the first stabilization device are sized to be the same or smaller than a size of the rods to clamp the rods in the channels.

22. The stabilization device of claim 12, wherein each bone anchoring device further comprises a fixation element configured to fix the position of the head in the receiving part.

23. The bone anchoring device of claim 12, further comprising a connector connecting an end of the first stabilization rod to an end of the second stabilization rod.

24. A method of attaching a stabilization device to bones or vertebrae, the stabilization device comprising a monolithic first stabilization rod, a monolithic second stabilization rod, a first bone anchoring device and a second bone anchoring device, each bone anchoring device comprising an anchoring element with an anchoring section for anchoring in a bone part or a vertebra and a head, a receiving part having a seat for receiving the head so that the head is polyaxially pivotable with respect to the receiving part, a first pressure element movable in the receiving part and configured to press onto the head to lock the angular position of the head relative to the receiving part, and wherein at least two guiding channels are provided within the receiving part for guiding the first stabilization rod and the second stabilization rod through the receiving part, the method comprising:
  attaching the first bone anchoring device to a bone or vertebra;
  attaching the second bone anchoring device to another bone or vertebra;
  connecting the first stabilization rod and the second stabilization rod to the first bone anchoring device;
  connecting the first stabilization rod and the second stabilization rod to the second bone anchoring device;
  wherein when the respective angular positions of the heads relative to the corresponding receiving parts of the bone anchoring devices are locked, the first stabilization rod and the second stabilization rod are fixedly connected to the first bone anchoring device, and the first stabilization rod and the second stabilization rod are slidably connected to the second bone anchoring device and are configured to contact the first pressure element of the second bone anchoring device.

25. The method of claim 24, further comprising mounting a spring element on each of the stabilization rods before connecting the stabilization rods to the bone anchoring devices, wherein the spring elements dampen the sliding movement of the stabilization rods relative to the second bone anchoring device.

26. A bone anchoring device comprising:
  an anchoring element with an anchoring section for anchoring in a bone part or a vertebra and a head;
  a monolithic one-piece continuous rod, wherein a first length of the rod and a second length of the rod each has a free end, and the first and second lengths of the rod have parallel longitudinal axes and are spaced apart from one another in a direction perpendicular to the longitudinal axes;
  a receiving part having a first end and a second end and a bore extending along an axis from the first end in the direction of the second end, wherein the receiving part has a seat in the bore for receiving the head so that the head is polyaxially pivotable with respect to the receiving part;
  a first pressure element movable in the bore of the receiving part and configured to press onto the head to lock the angular position of the head relative to the receiving part;
  wherein at least two guiding channels are provided within the bore of the receiving part for guiding the first length of the rod and the second length of the rod through the receiving part; and
  wherein when the angular position of the head relative to the receiving part is locked, the rod is slidably connected to the receiving part and is configured to contact the first pressure element.

27. A bone anchoring device comprising:
  an anchoring element with an anchoring section for anchoring in a bone part or a vertebra and a head;
  a monolithic first stabilization rod section and a monolithic second stabilization rod section;
  a receiving part having a first end and a second end and a bore extending along an axis from the first end in the direction of the second end, wherein the receiving part has a seat in the bore for receiving the head so that the head is polyaxially pivotable with respect to the receiving part;
  a first pressure element movable in the bore of the receiving part and configured to press onto the head to lock the angular position of the head relative to the receiving part;
  wherein at least two guiding channels are provided within the bore of the receiving part for guiding the first stabilization rod section and the second stabilization rod section through the receiving part;
  wherein when the first stabilization rod section and the second stabilization rod section are guided through the receiving part with the guiding channels, the first stabilization rod section and the second stabilization rod section each extends through an entire length of the receiving part, wherein the rod sections are entirely spaced apart from each other in the receiving part; and wherein when the angular position of the head relative to the receiving part is locked, the first stabilization rod section and the second stabilization rod section are slidably connected to the receiving part and are configured to contact the first pressure element.

* * * * *